US012774998B2

(12) United States Patent
Lim et al.

(10) Patent No.: US 12,774,998 B2
(45) Date of Patent: Oct. 27, 2026

(54) FOOD TEXTURE MEASURING APPARATUS AND FOOD TEXTURE MEASURING METHOD

(71) Applicant: CJ CHEILJEDANG CORPORATION, Seoul (KR)

(72) Inventors: Joo Hee Lim, Seoul (KR); Sang-Euii Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 334 days.

(21) Appl. No.: 18/577,144

(22) PCT Filed: Nov. 9, 2022

(86) PCT No.: PCT/KR2022/017558
§ 371 (c)(1),
(2) Date: Jan. 5, 2024

(87) PCT Pub. No.: WO2023/101249
PCT Pub. Date: Jun. 8, 2023

(65) Prior Publication Data
US 2024/0319158 A1 Sep. 26, 2024

(30) Foreign Application Priority Data
Nov. 30, 2021 (KR) ........................ 10-2021-0169439

(51) Int. Cl.
*G01N 33/02* (2006.01)
*G01N 3/06* (2006.01)
*G01N 3/42* (2006.01)

(52) U.S. Cl.
CPC ............. *G01N 33/02* (2013.01); *G01N 3/066* (2013.01); *G01N 3/42* (2013.01)

(58) Field of Classification Search
CPC ........... G01N 33/02; G01N 3/066; G01N 3/42
USPC ........................................................... 73/781
See application file for complete search history.

(56) References Cited

U.S. PATENT DOCUMENTS

| | | | | |
|---|---|---|---|---|
| 3,732,727 | A | 5/1973 | Hinnergardt et al. | |
| 4,007,632 | A | 2/1977 | Segars | |
| 2022/0236161 | A1* | 7/2022 | Gorey | G01N 11/00 |

FOREIGN PATENT DOCUMENTS

| | | | | |
|---|---|---|---|---|
| CN | 1571533 A | | 1/2005 | |
| DE | 600 31 431 T2 | | 9/2007 | |
| EP | 1219947 A1 | * | 7/2002 | G01N 3/08 |
| JP | 2016-045168 A | | 4/2016 | |

(Continued)

OTHER PUBLICATIONS

L.C. Hinnergardt and J. M. Tuomy, "A penetrometer test to measure meat tenderness", Published in Journal of Food Science, vol. 35, 1970, pp. 312-314 (Year: 1970).*

(Continued)

*Primary Examiner* — Peter J Macchiarolo
*Assistant Examiner* — John M Royston
(74) *Attorney, Agent, or Firm* — Morgan, Lewis & Bockius LLP

(57) ABSTRACT

The present invention relates to a food texture measuring apparatus and a food texture measuring method, and more specifically to a food texture measuring apparatus which is capable of simultaneously measuring texture patterns of a subject and capable of measuring texture according to the size and shape of the subject.

11 Claims, 10 Drawing Sheets

(56) References Cited

FOREIGN PATENT DOCUMENTS

| | | | |
|---|---|---|---|
| KR | 10-2017-0069143 | A | 6/2017 |
| KR | 10-2061419 | B1 | 12/2019 |

OTHER PUBLICATIONS

Szczesniak, "Instrumental Methods of Texture Measurement", Food Technology, vol. 26, No. 1, Jan. 1972, pp. 50-56.

Extended European Search Report issued in corresponding European Patent Application No. 22901607.6, dated Sep. 26, 2024.

International Search Report issued in corresponding International Patent Application No. PCT/KR2022/017558 dated Feb. 14, 2023.

Hinnergardt et al., "A Penetrometer Test to Measure Meattenderness", Journal of Food Science, 1970,vol. 35, No. 3, 1970, pp. 312-315.

Office Action issued in corresponding Chinese Patent Application No. 202280044562.9, dated Jan. 24, 2026.

* cited by examiner

FOOD TEXTURE MEASURING APPARATUS AND FOOD TEXTURE MEASURING METHOD

TECHNICAL FIELD

The present invention relates to a food texture measuring apparatus and a food texture measuring method, and more specifically to a food texture measuring apparatus which is capable of simultaneously measuring texture patterns of a subject and capable of measuring texture according to the size and shape of the subject.

BACKGROUND ART

As a method for measuring the texture of food, there is a predetermined texture analysis apparatus. Such texture analysis apparatus can analyze the texture of various types of foods by using a variety of probes.

Meanwhile, after food is cooked, textures may appear different from each other depending on the part. For example, in the case of pizza, the hardness of the texture may appear different according to the position of the pizza dough. FIG. 11 shows texture of such a pizza dough, showing that the center has medium strength, the sides have high strength, and a portion between the center and the sides (middle) has low strength.

Depending on these texture characteristics, the taste for food may change. Thus, food companies and food research institutes are conducting research to increase or decrease the difference in texture according to parts of food by improving raw materials and processing processes of food.

In order to conduct such research, an apparatus capable of measuring texture characteristics quickly and accurately according to the size and shape of food is required.

Patent Literature

Korean Patent Registration Laid-open Publication No. 10-2061419

DETAILED DESCRIPTION OF THE INVENTION

Technical Problem

The present invention provides a food texture measuring module and a food texture measuring apparatus, which are capable of individually specifying texture of food according to sections and simultaneously measuring texture in one section so that a texture of food can be accurately and quickly measured.

Technical Solution

According to an aspect of the present invention, there is provided a food texture measuring apparatus including: a frame in which a power device is built; a stage module, which is connected to the frame and on which a subject is put; and a probe module, which is connected to the frame, located on the stage module and of which a position is changed, wherein the probe module includes: a probe plate having a predetermined area; pins arranged on a bottom surface of the probe plate; and a connector connecting the probe plate and the power device to each other, the probe plate and the pins are integrally displaced, and the pins are configured to measure texture of the subject put on the stage module.

The frame may include: a base; a head disposed on the base; and a neck connecting the base and the head to each other and having a predetermined height, the stage module may be connected to the base, and the probe module may be connected to the head.

The frame may include a guide beam extending in at least one direction, and the probe module may include a guide block connecting the probe plate and the guide beam to each other, and displacement of the probe module may be guided by the guide beam and the guide block.

The probe module may be connected to the head, and a connection position of the probe module and the head may be optionally changed.

The probe module may include a linkage part connecting the head and the connector to each other, and a position where the connector is connected to the linkage part and a position where the head is connected to the linkage part may be changed.

The frame may include a connection jig connected to the base and protruding toward at least one side, a plurality of connection jigs may be provided, a distance between the plurality of connection jigs may be changed, the stage module may be connected to the connection jig, and a size of the stage module connected to the connection jig may be optionally changed according to the distance between the connection jigs.

A plurality of pins may be provided, and the plurality of pins may have a predetermined arrangement according to texture patterns of food to be measured.

The stage module may include a stage plate having a predetermined area, the stage plate may include one or more stage holes penetrating the stage plate vertically, the pins may be located in the stage holes, and, when the probe module descends, the pins may be capable of being put into the stage holes.

According to another aspect of the present invention, there is provided a food texture measuring method by using a food texture measuring apparatus, the food texture measuring apparatus including a frame in which a power device is built; a stage module, which is connected to the frame and on which a subject is put; and a probe module, which is connected to the frame, located on the stage module and of which a position is changed, the food texture measuring method including: a first step of determining a size of a subject; a second step of selecting the stage module and the probe module; a third step of installing the selected stage module and probe module at the frame; and a fourth step of measuring texture of the subject.

The third step may include arranging the stage module and the probe module so that a center of the stage module and a center of the probe module are arranged to be positioned on a straight line with each other.

The probe module may include: a probe plate having a predetermined area; and pins arranged on a bottom surface of the probe plate, the stage module may include a stage plate having a predetermined area, the stage plate may include one or more stage holes penetrating the stage plate vertically, the pins may be located in the stage holes, and, when the probe module descends, the pins may be capable of being put into the stage holes, and the fourth step may include lowering the probe module and allowing the pins to penetrate the subject and the pins to be put into the stage holes.

The probe module may include: a probe plate having a predetermined area; pins arranged on a bottom surface of the probe plate; a connector connecting the probe plate and the power device to each other; and a linkage part connecting the head and the connector to each other, the linkage part may be configured in such a way that a position where the connector is connected to the linkage part and a position where the head is connected to the linkage part may be changed, and the third step may include changing a position of the probe module by using the linkage part.

Effects of the Invention

According to an embodiment of the present invention, since the arrangement of pins is an arrangement corresponding to texture patterns of a subject, texture patterns of the subject can be appropriately measured.

In addition, since the size and shape of a stage module and the size, shape, and position of a probe module can be changed, a texture measuring apparatus can be properly implemented according to the specifications of the subject.

In addition, a stage hole is provided in a stage plate of the stage module, and the stage hole and the pins may have arrangements corresponding to each other. According to this, an empty space due to the stage hole is located below a texture measurement point (a point where the subject is in contact with the pins) of the subject to be measured. Thus, when the texture of food is measured by the pin, resistance due to the stage plate may not be encountered. For example, as the probe module located on the stage module descends, an examination environment in which the pins penetrate the subject can be created. Thus, the texture of the subject (variation in force from contact with the pins to penetration) can be accurately measured according to the purpose.

MODE OF THE INVENTION

Hereinafter, the present invention will be described in detail by describing embodiments of the present invention with reference to the accompanying drawings.

Figure 1:
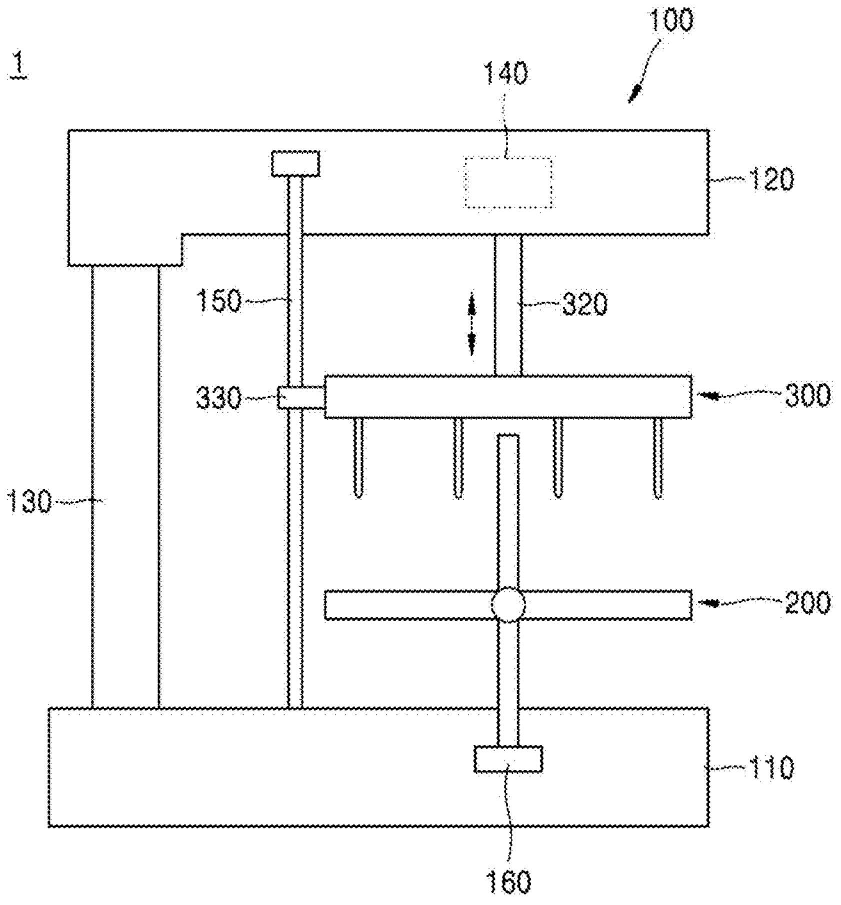
FIGS. 1 and 2 are views illustrating a food texture measuring apparatus according to an embodiment of the present invention.
Figure 2:
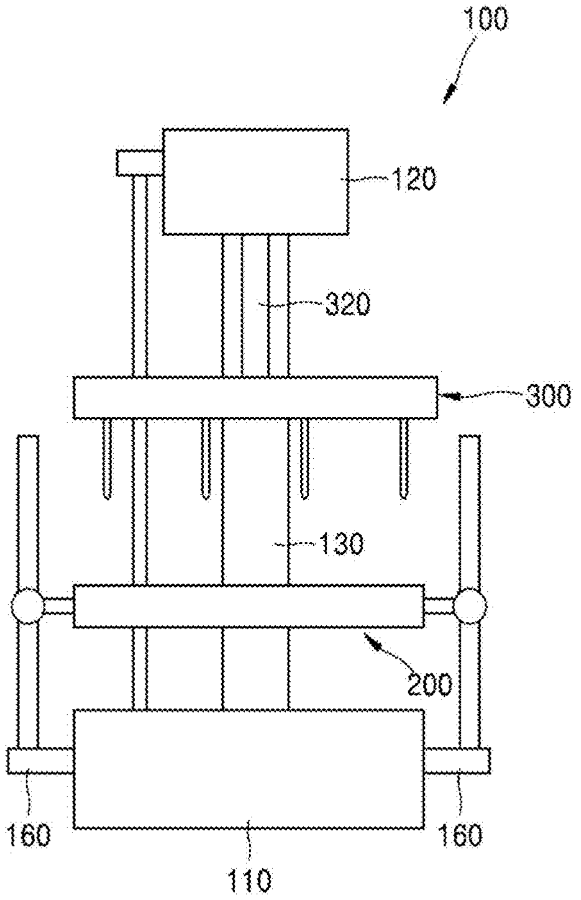

FIGS. 1 and 2 are views illustrating a food texture measuring apparatus 1 according to an embodiment of the present invention.

The food texture measuring apparatus 1 according to an embodiment of the present invention includes a frame 100, a stage module 200 on which a subject is put, and a probe module 300 that is placed on the stage module 200 and is displaceable.

<Frame 100>

According to an embodiment, the frame 100 may include a base 110, a head 120 disposed on the base 110, and a neck 130 that connects the base 110 and the head 120 to each other and extends vertically. Thus, the frame 100 may have a U-shaped structure as a whole.

A power device 140 may be built in the frame 100. The power device 140 is a device that can displace the probe module 300. The power device 140 may be, for example, a servo motor or the like, and the present invention is not limited thereto. In FIG. 1, the power device 140 is built in the head 120. However, the present invention is not limited thereto.

According to an embodiment, the frame 100 may further include a guide beam 150 that is connected to the probe module 300 and guides displacement of the probe module 300.

In an example, the guide beam 150 may include a beam connected between the base 110 and the head 120. The guide beam 150 may be an upright beam, and the present invention is not limited thereto.

According to an embodiment, the frame 100 may further include a connection jig 160. The connection jig 160 may be an intermediate member that connects the stage module 200 and the base 110 to each other. According to an embodiment, the connection jig 160 may include a finger 162 that protrudes toward at least one side of the base 110, and a connection beam 164 that extends in the finger 162. The stage module 200 to be described later may be connected to the connection beam 164.

A specific embodiment of the connection jig 160 will be described in the description relating to the stage module 200 to be described later.

<Stage Module 200>

Figure 3:
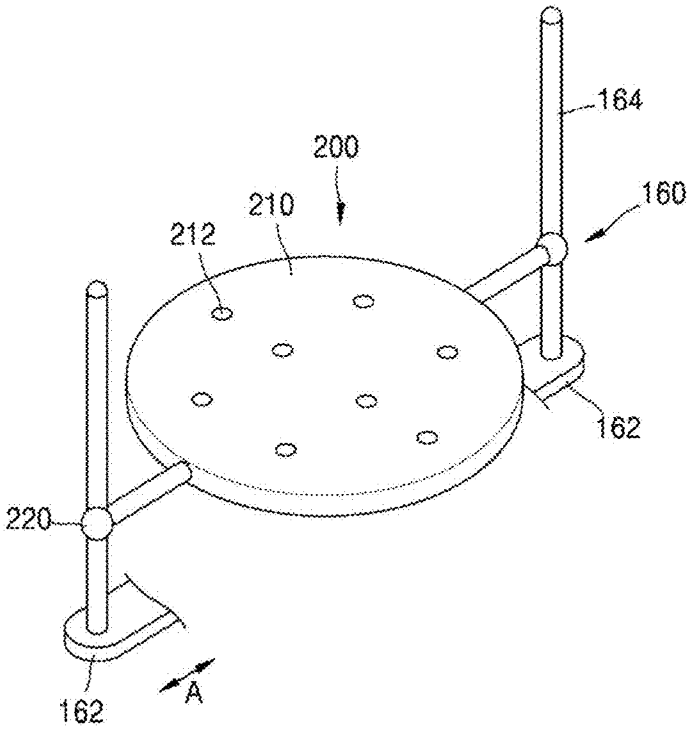
FIGS. 3 and 4 are views illustrating a stage module of a food texture measuring apparatus according to an embodiment of the present invention.
Figure 4:
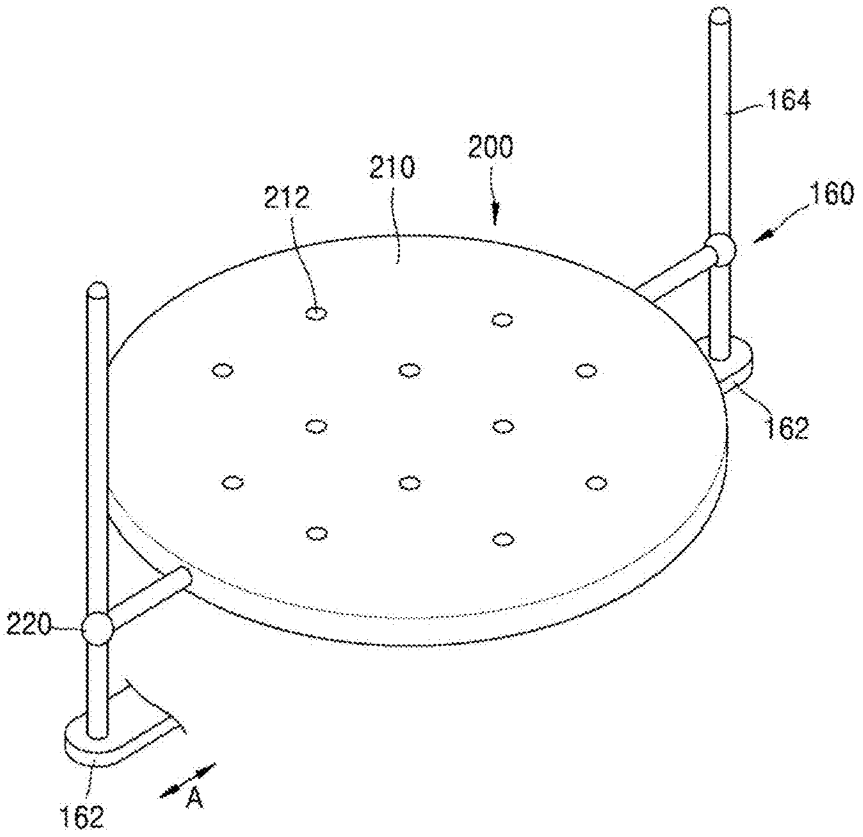
Figure 5:
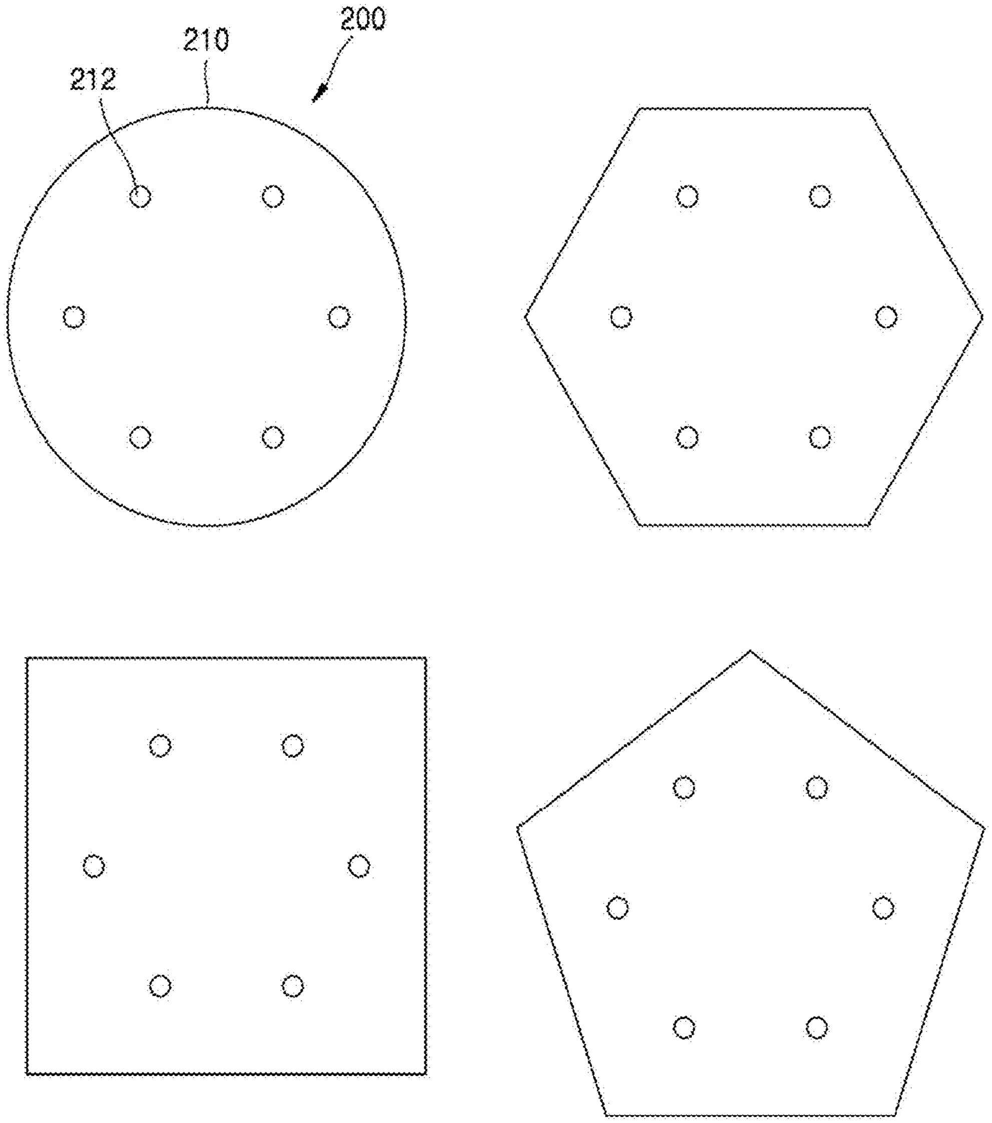
FIG. 5 is a view illustrating the shape of a stage module of a food texture measuring apparatus according to an embodiment of the present invention.

FIGS. 3 and 4 are views illustrating the stage module 200 of the food texture measuring apparatus 1 according to an embodiment. FIG. 5 is a view illustrating the shape of the stage module 200 of the food texture measuring apparatus 1 according to an embodiment.

The stage module 200 may include a stage plate 210 having a predetermined area. A subject that is a texture measurement target may be put on the stage plate 210.

The stage plate 210 is a member having predetermined thickness and area. The material of the stage plate 210 is not limited and may include a synthetic resin or a metal material.

The shape of the stage plate 210 may have various shapes according to texture patterns of the subject to be measured. For example, the stage plate 210 may have a shape, such as a circle, a triangle, a square, or a pentagon, according to the arrangement of texture patterns of the subject. An example of the shape of the stage plate 210 described above is shown in FIG. 5. However, the matters shown in the drawings are only examples, and the present invention is not limited thereto.

One or more stage holes 212 penetrating the stage plate 210 vertically may be provided in the stage plate 210.

There may be a plurality of stage holes 212. The plurality of stage holes 212 may have an arbitrary arrangement according to texture patterns of the subject to be measured.

For example, the stage holes 212 may be arranged radially around the center of the probe plate 310, or may be respectively arranged at positions of vertices of a predetermined figure.

According to an embodiment, at least one side of the stage plate 210 may be provided with a predetermined connection portion 220 connecting the frame 100 and the stage plate 210 to each other. Specifically, the connection portion 220 may be connected to the connection beam 164 of the connection jig 160 described above.

Connection between the connection jig 160 and the connection portion 220 and changing the size of the stage plate 210 thereby will be described as below.

According to an embodiment, a plurality of connection jigs 160 may be provided in the frame 100, and a distance between the plurality of connection jigs 160 may be changed. For example, as the arrow A shown in FIGS. 3 and 4, the connection jig 160 may protrude from the base 110 in one direction, wherein a protruding width of the connection jig 160 may be changed.

For example, according to an embodiment, the connection jig 160 may include a finger 162 that protrudes toward at least one side of the base 110, and a connection beam 164 that extends to the finger 162. The protruding width of the connection jig 160 is changed so that a distance between the connection beams 164 located on the finger 162 can be changed.

The stage module 200 is connected to the connection jig 160. Specifically, the stage module 200 may be connected to the connection beam 164. In this case, the distance between the connection beams 164 is changed so that the size of the stage module 200 can be optionally changed.

For example, as shown in FIG. 4, when the distance between the connection beams 164 is set to be relatively large, the stage module 200 having a large size may be connected to the connection jig 160. Thus, the texture of the subject having a large area can be measured. In contrast, when the distance between the connection beams 164 is set to be relatively small, as shown in FIG. 3, the stage module 200 having a small size can be connected to the connection jig 160. Thus, the texture of the subject having a small area can be measured.

<Probe Module 300>

Figure 6:
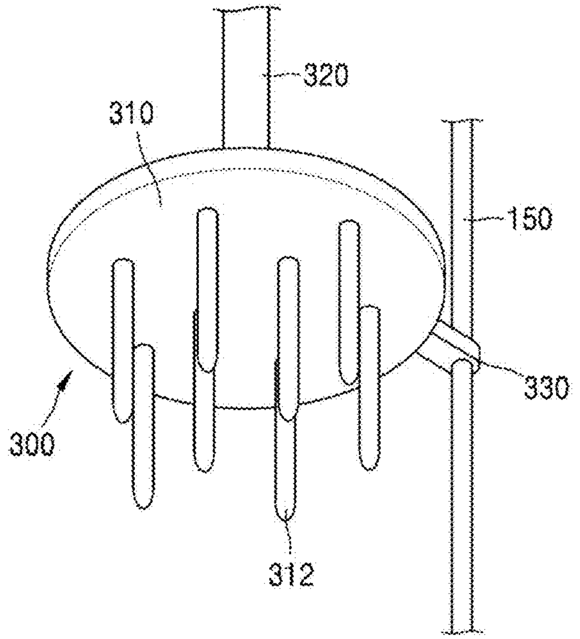
FIG. 6 is a view illustrating a probe module of a food texture measuring apparatus according to an embodiment of the present invention.
Figure 7:
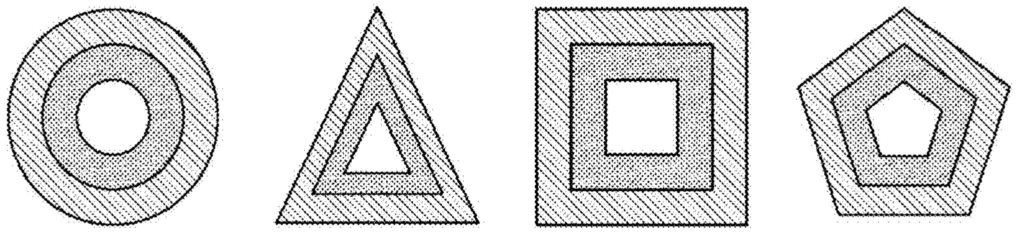
FIG. 7 is a view illustrating an example of the arrangement of a probe module of a food texture measuring apparatus according to an embodiment of the present invention.
Figure 8:
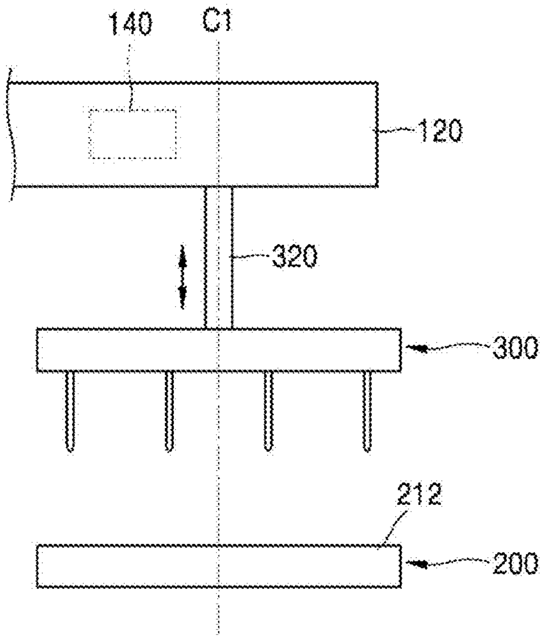
FIGS. 8 and 9 are views illustrating connection between a frame and a probe module of a food texture measuring apparatus according to an embodiment of the present invention.
Figure 9:
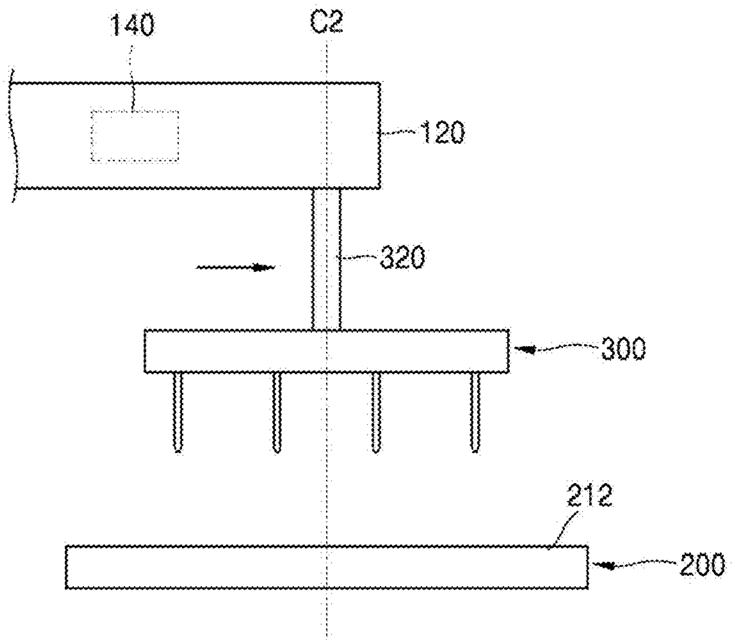
Figure 10:
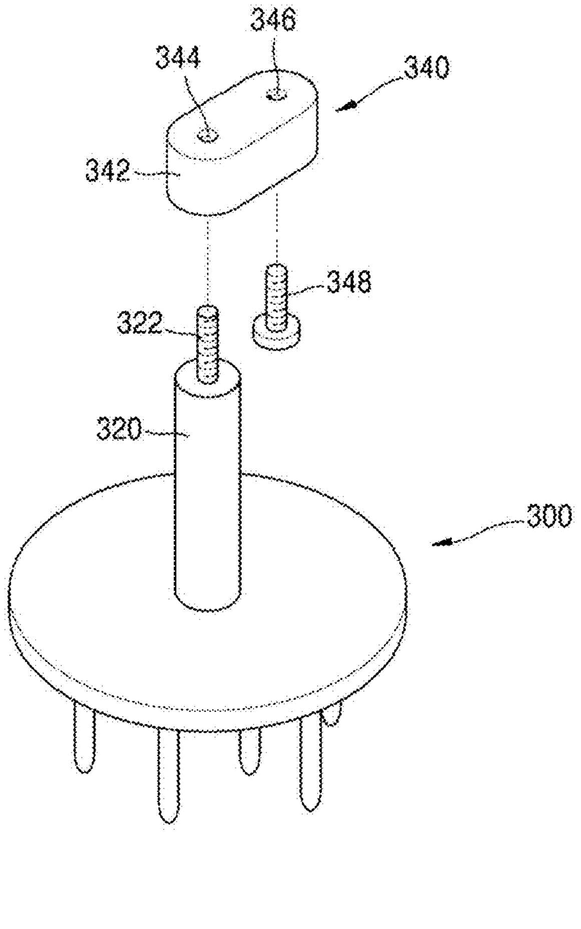
FIG. 10 is a view illustrating a probe module of a food texture measuring apparatus according to an embodiment of the present invention.
Figure 11:
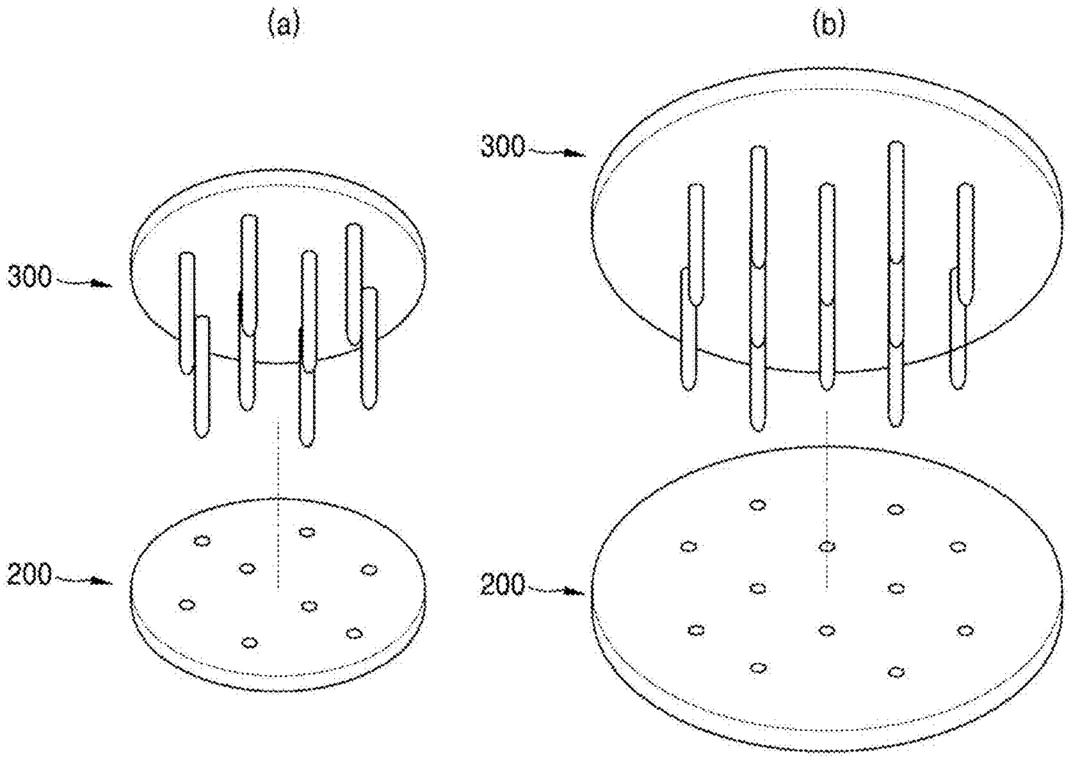
FIG. 11 is a view illustrating the relationship between a stage module and a probe module of a food texture measuring apparatus according to an embodiment of the present invention.
Figure 12:
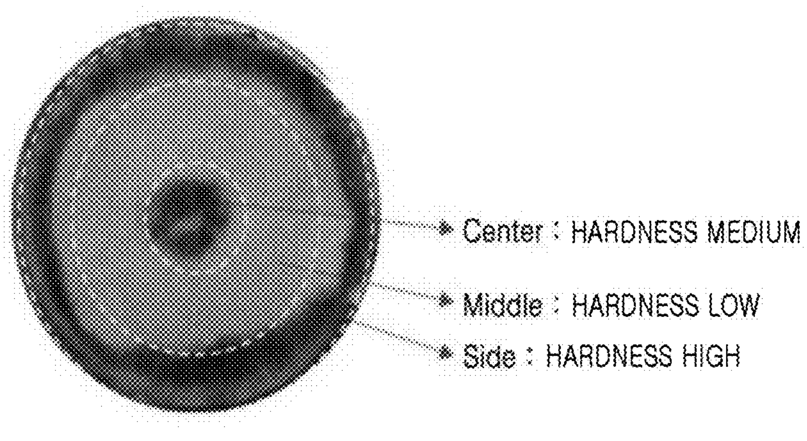
FIG. 12 is a view illustrating an example of a texture of a pizza dough.

FIG. 6 is a view illustrating the probe module 300 of the food texture measuring apparatus 1 according to an embodiment of the present invention. FIG. 7 is a view illustrating an example of the arrangement of the probe module 300 of the food texture measuring apparatus according to an embodiment of the present invention. FIGS. 8 and 9 are views illustrating connection between the frame 100 and the probe module 300 of the food texture measuring apparatus 1 according to an embodiment of the present invention. FIG. 10 is a view illustrating the probe module 300 of the food texture measuring apparatus 1 according to an embodiment of the present invention. FIG. 11 is a view illustrating the relationship between the stage module 200 and the probe module 300 of the food texture measuring apparatus 1 according to an embodiment of the present invention.

The probe module 300 may include the probe plate 310 having a predetermined area, pins 312 arranged on the bottom surface of the probe plate 310, and a connector 320 that connects the probe plate 310 and the power device 140 to each other.

The probe plate 310 is a member having a predetermined thickness and area. The material of the probe plate 310 is not limited thereto and may include a synthetic resin or a metal material.

The shape of the probe plate 310 may have various shapes according to texture patterns of the subject to be measured. For example, the stage plate 210 may have a shape, such as a circle, a triangle, a square, or a pentagon, according to the arrangement of texture patterns of the subject.

The pins 312 may be a predetermined sensor that is capable of measuring the texture of the subject. For example, the pins 312 may measure the viscosity, moisture content, hardness, and the like of food that is the subject. In order to measure such a texture, the pins 312 may include an appropriate sensor unit. However, the present invention is not limited thereto.

The pins 312 are arranged on the bottom surface of the probe plate 310. The pins 312 may be integrally connected to the probe plate 310. Thus, when the probe plate 310 is displaced, the pins 312 may be displaced integrally with the probe plate 310. For example, when the probe plate 310 descends, the pins 312 descend together, and when the probe plate 310 ascends, the pins 312 may ascend together.

The pins 312 may have various forms and shapes. That is, the shape of the pins 312 is not limited to the shape shown in the drawings.

A plurality of pins 312 may be provided. The plurality of pins 312 may have an arbitrary arrangement.

According to an embodiment, the plurality of pins 312 may have an arrangement according to established rules. In an example, a distance between the adjacent pins 312 may be the same. In another example, a plurality of pins 312 may have a predetermined polygonal or circular arrangement shape around the center of the probe plate 310. In addition, in another example, the plurality of pins 312 may have the polygonal or circular arrangement and may also have a multi-layered arrangement. For example, as shown in FIG. 7, the probe module 300 may have a structure in which the pins 312 are arranged in an inner region of a relatively large polygon or circular shape (outer layer) and the pins 312 are arranged in an inner region of a relatively small polygon or circular shape (inner layer). However, the present invention is not limited thereto.

As described above, a plurality of stage holes 212 may be provided in the stage module 200, and the arrangement of the plurality of stage holes 212 may be determined according to texture patterns of the subject to be measured. In response, the pins 312 may be in plural, and a plurality of pins 312 may have an arrangement according to texture patterns of the subject to be measured. That is, the arrangement of the pins 312 and the arrangement of the stage holes 212 may correspond to each other.

For example, the pins 312 may be arranged radially around the center of the probe plate 310, or may also be respectively arranged at positions of vertices of a predetermined figure. The arrangement of the pins 312 may be determined according to texture patterns of the subject to the measured.

In this case, according to an embodiment, the size of each of the pins 312 may be smaller than the size of each of the stage holes 212. Thus, the pins 312 may be put into the stage holes 212.

The connector 320 may be connected to the probe plate 310 and may be a connection unit that connects the probe plate 310 and the frame 100 to each other. For example, the connector 320 may be a predetermined beam that is located at the center of the probe plate 310 and extends vertically.

According to an embodiment, a guide block 330 may be provided at one side of the probe plate 310. The guide block 330 may be a predetermined block connected to the guide beam 150 to be described below.

The guide block 330 may be connected to the guide beam 150 and may be displaced along the guide beam 150. For example, the guide block 330 may have guide holes through which the guide beam 150 passes.

As described above, the guide block 330 and the guide beam 150 are provided so that the displacement of the probe module 300 can be stably guided.

According to an embodiment, the probe module 300 may be connected to a head 120 of the frame 100. In this case, a connection position between the probe module 300 and the head 120 can be optionally changed.

For example, when a position where a neck 130 of the frame 100 is located, is referred to as rear, connection positions C1 and C2 between the probe module 300 and the head 120 may be relatively rear positions, as shown in FIG. 8, and may be relatively front positions, as shown in FIG. 9. That is, a distance between the central point of the probe module 300 and the neck 130 can be relatively changed.

Thus, when the area of the subject is large and the size of the probe plate 310 provided in the probe module 300 is set to be large, the distance between the neck 130 and the center point of the probe module 300 can be increased. Thus, the probe module 300 having an appropriate size according to the size of the subject can be used.

A unit and a method for changing the connection position of the probe module 300 are not limited thereto. For example, a predetermined sliding device that changes the position of the probe module 300 in a state where the probe module 300 is connected to the head 120, may also be provided in the frame 100. Alternatively, a plurality of connection units (e.g., screw holes or the like) may be provided in the head 120, and the probe module 300 may also be optionally connected to the plurality of connection units.

According to an embodiment, the probe module 300 may include a predetermined linkage part 340 that connects the frame 300 and the connector 320 to each other. Furthermore, the connection position of the probe module 300 can be changed according to selection of the linkage part 340.

For example, as shown in FIG. 10, the linkage part 340 may include a link block 342 having a plurality of connection holes 344 and 346 formed therein, and a connection screw 348 that connects the link block 342 to the head 120. The connector 320 may be connected to one of the connection holes 344 and 346. In an example, a connection end 322 having a predetermined male screw formed therein may be provided at an upper end of the connector 320. Furthermore, the connection screw 348 may pass through one connection hole 346 and may be connected to the head 120 of the frame 100. Thus, a connection position (accurately, the position of the connector 320) between the probe module 300 and the frame 100 may be changed.

According to an embodiment, the probe module 300 may be located at an arbitrary position other than the center of the stage module 200. Thus, texture measurement of an arbitrary portion of the subject put on the stage module 200 can be performed.

Hereinafter, the operation and effects of the food texture measuring apparatus 1 according to the present invention will be described.

In a state where the subject is put on the stage module 200, the probe module 300 may descend. In this case, when the pins 312 of the probe module 300 make contact with the subject, the texture of the subject can be measured. As described above, since the arrangement of the pins 312 is an arrangement corresponding to texture patterns of the subject, the texture patterns of the subject can be properly measured.

In addition, since the size and shape of the stage module 200 and the size, shape, and position of the probe module 300 can be changed, the texture measuring apparatus 1 can be properly implemented according to the specifications of the subject.

In addition, since the connection position of the probe module 300 may be different, texture measurement at several positions of the subject can be optionally performed.

In addition, the stage holes 212 are provided in the stage plate 210 of the stage module 200, and the stage holes 212 and the pins 312 may have an arrangement in which they correspond to each other. That is, the pins 312 and the stage holes 212 may be located in a straight line in a vertical direction with each other.

According to this, an empty space is located under a texture measurement point (a point located directly below the pins 312) of the subject to be measured due to the stage holes 212. Thus, when the texture of food is measured by the pins 312, resistance due to the stage plate 210 may not be received. For example, as the probe module 300 located on the stage module 200 descends, an inspection environment in which the pins 312 penetrate the subject, may be established. According to this, the texture (for example, the degree of elongation from when the pins 312 make contact until they penetrate) of the subject can be accurately measured according to purposes.

In addition, in this case, according to an embodiment, the size of the pins 312 may be smaller than the size of the stage holes 212. Thus, when the pins 312 drop, the pins 312 can be put into the stage holes 212. Thus, a jamming phenomenon of the pins 312 may not occur.

In a food texture measuring method by using a food texture measuring apparatus according to the present invention, the texture of each position of food that is a subject can be simultaneously measured. Furthermore, the texture (e.g., changes in force from when the pins 312 make contact until they penetrate) of the subject can be accurately measured according to purposes.

The food texture measuring apparatus and the food texture measuring method according to embodiments of the present invention may be properly used, in particular, in texture measurement of wide and flat food such as a pizza dough, for example. In particular, since the pizza dough has a little viscosity (characteristics such as chewy, weeping or the like), the above-described properties can be effectively measured in a procedure in which, when the pins 312 make contact the pizza dough and penetrate the pizza dough, the pins 312 are put into the stage holes 212.

Figure 13:
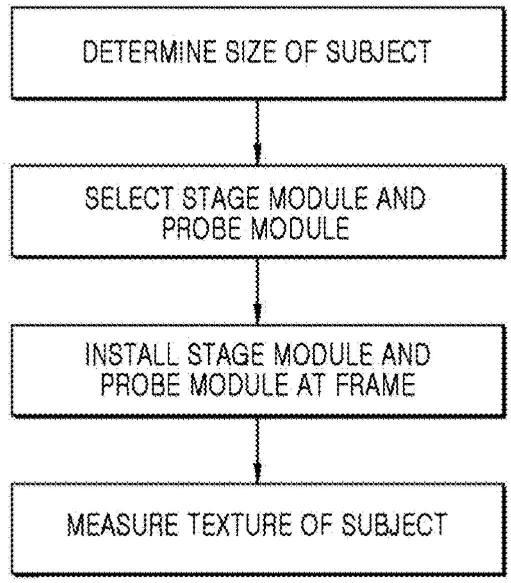
FIG. 13 is a flowchart illustrating the order of a food texture measuring method by using a food texture measuring apparatus according to an embodiment of the present invention.

FIG. 13 is a flowchart illustrating the order of a food texture measuring method by using a food texture measuring apparatus according to an embodiment of the present invention.

Hereinafter, the food texture measuring method according to an embodiment of the present invention will be described.

The food texture measuring method according to an embodiment of the present invention is described as follows.

First step: first, the size of a subject is determined. The subject may be food having predetermined area and thickness, such as a pizza dough. Meanwhile, the subject may be a product that can be cooked in a cooking appliance such as a microwave or an air fryer, and thus, preferably, may have a size acceptable in the cooking appliance. In an example, the subject may have a length of 3 to 10 inches.

Second step: a stage module 200 and a probe module 300 are selected according to the determined size of the subject. For example, when the size of the subject is large, the stage module 200 and the probe module 300 each having a large area can be selected.

Third step: the selected stage module 200 and probe module 300 are installed at the frame 100.

In this case, the center of the stage module 200 and the center of the probe module 300 may be arranged to be positioned on a straight line with each other. Meanwhile, according to another embodiment, the present invention is not necessarily limited thereto, and the probe module 300 is placed at one position of the stage module 200 so that the texture of an arbitrary part of the subject can also be measured.

In this case, according to an embodiment, the probe module 300 includes a linkage part 340, and the position (a connection position between the probe module 300 and the head 120) of the probe module 300 can be optionally changed by the linkage part 340. Thus, the position of the probe module 300 can be changed by using the linkage part 340, and the probe module 300 can also be placed at an arbitrary position of the stage module 200.

Fourth step: the texture of the subject is measured.

In this case, the stage module 200 includes a stage plate 210 having a predetermined area, and the stage plate 210 may include one or more stage holes 212 that penetrate the stage plate 210 vertically. Furthermore, the pins 312 may be located in the stage holes 212, and when the probe module 300 descends, the pins 312 may be put into the stage holes 212.

Thus, in the fourth step of measuring the texture of the subject, a procedure in which the probe module 300 descends, the pins 312 penetrate the subject and are put into the stage holes 212, can be performed. According to this, the texture (changes in force from when the pins make contact until they penetrate) of the subject can be accurately measured according to purposes.

The food texture measuring apparatus according to an embodiment of the present invention can be utilized in texture measurement of various food such as breads, confectionary, tortillas, and the like. Furthermore, when, as a result of performing measurement, data that do not meet the standard value are derived, factors (material, a mixing process, heating temperature and time, and the like) of the subject can be changed and supplemented. In addition, after changing these factors, texture can be measured again in the same environment (the use of the same probe) so that the accuracy of texture measurement can be enhanced. In addition, texture measurement can be conveniently performed for each area of the same food according to user's selection (configuration change and the like). Furthermore, according to texture measurement of these food and measurement results, the texture of each food can be optimized for distribution and cooking.

While the present invention has been particularly shown and described with reference to exemplary embodiments thereof, it will be understood by those of ordinary skill in the art that various changes in form and details may be made therein without departing from the spirit and scope of the present invention as defined by the following claims.

EXPLANATION OF REFERENCE NUMERALS

1: food texture measuring apparatus
100: frame
110: base
120: head
130: neck
140: power device
150: guide beam
160: connection jig
162: finger
164: connection beam
200: stage module
210: stage plate
212: stage holes
220: connection portion
300: probe module
310: probe plate
312: pins
320: connector
322: connection end
330: guide block
340: linkage part
342: link block
344,346: connection hole
348: connection screw

The invention claimed is:

1. A food texture measuring apparatus comprising:
a frame in which a power device is built;
a stage module, which is connected to the frame and on which a subject is put; and
a probe module, which is connected to the frame, located on the stage module and of which a position is changed,
wherein the probe module comprises: a probe plate having a predetermined area; pins arranged on a bottom surface of the probe plate; and a connector connecting the probe plate and the power device to each other,
the probe plate and the pins are integrally displaced,
the pins are configured to measure texture of the subject put on the stage module,
the frame comprises a base and connection jigs installed on the base,
the connection jigs comprise: fingers respectively protruding from both sides of the base, the protruding width of which is variable; and a connection beam extending upward from each finger, a distance between the connection beams varying according to the change in the protruding width of the fingers; and
the stage module having a size corresponding to the distance between the connection beams is positioned between the connection beams, and both sides thereof are respectively connected to the connection beams.

2. The food texture measuring apparatus of claim 1, wherein the frame further comprises:
a head disposed on the base; and
a neck connecting the base and the head to each other and having a predetermined height,
the stage module is connected to the base, and
the probe module is connected to the head.

3. The food texture measuring apparatus of claim 1, wherein the frame comprises a guide beam extending in at least one direction, the probe module comprises a guide block connecting the probe plate and the guide beam to each other, and displacement of the probe module is guided by the guide beam and the guide block.

4. The food texture measuring apparatus of claim 2, wherein the probe module is connected to the head, and a connection position of the probe module and the head is optionally changed.

5. The food texture measuring apparatus of claim 4, wherein the probe module comprises a linkage part connecting the head and the connector to each other, and a position where the connector is connected to the linkage part and a position where the head is connected to the linkage part are changed.

6. The food texture measuring apparatus of claim 1, wherein a plurality of pins are provided, and the plurality of pins have a predetermined arrangement according to texture patterns of food to be measured.

7. The food texture measuring apparatus of claim 1, wherein the stage module comprises a stage plate having a predetermined area, the stage plate comprises one or more stage holes penetrating the stage plate vertically, and the pins are located in the stage holes, and, when the probe module descends, the pins are capable of being put into the stage holes.

8. A food texture measuring method by using a food texture measuring apparatus, the food texture measuring apparatus including a frame in which a power device is built; a stage module, which is connected to the frame and on which a subject is put; and a probe module, which is connected to the frame, is located on the stage module and of which position is changed, the food texture measuring method comprising:

a first step of determining a size of a subject;

a second step of selecting the stage module and the probe module;

a third step of installing the selected stage module and probe module at the frame; and a fourth step of measuring texture of the subject, wherein the probe module comprises a probe plate having a predetermined area; pins arranged on a bottom surface of the probe plate; a connector connecting the probe plate and the power device to each other; and a linkage part connecting a head and the connector to each other, and the linkage part is configured in such a way that a position where the connector is connected to the linkage part and a position where the head is connected to the linkage part are changed.

9. The food texture measuring method of claim 8, wherein the third step comprises arranging the stage module and the probe module so that a center of the stage module and a center of the probe module are arranged to be positioned on a straight line with each other.

10. The food texture measuring method of claim 8, wherein the probe module comprises:

a probe plate having a predetermined area; and pins arranged on a bottom surface of the probe plate, the stage module comprises a stage plate having a predetermined area, the stage plate comprises one or more stage holes penetrating the stage plate vertically, the pins are located in the stage holes, and, when the probe module descends, the pins are capable of being put into the stage holes, and the fourth step comprises lowering the probe module and allowing the pins to penetrate the subject and the pins to be put into the stage holes.

11. The food texture measuring method of claim 8, wherein the third step comprises changing a position of the probe module by using the linkage part.

* * * * *